(12) United States Patent
Calemma et al.

(10) Patent No.: US 7,560,408 B2
(45) Date of Patent: Jul. 14, 2009

(54) CATALYTICALLY ACTIVE AMORPHOUS POROUS SOLID AND PROCESS FOR ITS PREPARATION

(75) Inventors: Vincenzo Calemma, San Donato Milanese-Milan (IT); Cristina Flego, Milan (IT); Luciano Cosimo Carluccio, San Donato Milanese-Milan (IT); Roberto Millini, Cerro Al Lambro-Milan (IT); Wallace Parker, Peschiera Borromeo-Milan (IT)

(73) Assignees: Eni S.p.A., Rome (IT); Enitecnologie S.p.A., San Donato Milanese (IT)

( * ) Notice: Subject to any disclaimer, the term of this patent is extended or adjusted under 35 U.S.C. 154(b) by 246 days.

(21) Appl. No.: 10/563,209

(22) PCT Filed: Jun. 25, 2004

(86) PCT No.: PCT/EP2004/006932

§ 371 (c)(1),
(2), (4) Date: May 25, 2006

(87) PCT Pub. No.: WO2005/002725

PCT Pub. Date: Jan. 13, 2005

(65) Prior Publication Data

US 2007/0010395 A1    Jan. 11, 2007

(30) Foreign Application Priority Data

Jul. 3, 2003   (IT) .......................... MI2003A1360

(51) Int. Cl.
| | |
|---|---|
| *B01J 21/02* | (2006.01) |
| *B01J 27/182* | (2006.01) |
| *B01J 21/00* | (2006.01) |
| *B01J 13/00* | (2006.01) |
| *C09K 3/00* | (2006.01) |
| *B01D 21/01* | (2006.01) |
| *C08J 3/02* | (2006.01) |
| *C01B 33/152* | (2006.01) |
| *C01B 33/155* | (2006.01) |
| *C01F 7/02* | (2006.01) |

(52) U.S. Cl. .................. 502/214; 502/202; 502/235; 502/238; 516/98; 516/111; 516/112

(58) Field of Classification Search .............. 502/202, 502/214, 235, 238; 516/98, 111, 112
See application file for complete search history.

(56) References Cited

U.S. PATENT DOCUMENTS

| | | | |
|---|---|---|---|
| 4,430,252 A |   | 2/1984 | Ryu |
| 4,673,559 A | * | 6/1987 | Derouane et al. ............ 423/701 |
| 5,139,989 A | * | 8/1992 | Chao et al. ................... 502/214 |
| 5,230,789 A | * | 7/1993 | Chao et al. .................... 208/46 |
| 5,879,655 A | * | 3/1999 | Miller et al. ................. 423/702 |
| 6,531,051 B1 | * | 3/2003 | Kasztelan et al. ......... 208/111.3 |

FOREIGN PATENT DOCUMENTS

| | | |
|---|---|---|
| EP | 0 529 923 | 3/1993 |
| EP | 0 748 652 | 12/1996 |
| EP | 1 101 813 | 5/2001 |
| JP | 07-204512 * | 8/1995 |
| JP | 2002-028491 | 1/2002 |

* cited by examiner

*Primary Examiner*—Patricia L Hailey
(74) *Attorney, Agent, or Firm*—Oblon, Spivak, McClelland, Maier & Neustadt, P.C.

(57) ABSTRACT

Amorphous porous solid of an acidic nature, with a controlled pore size, essentially consisting of a mixed oxide of silicon, aluminum and phosphorous, having a surface area of at least 200 m²/g, which can be used as a catalyst or active carrier of a catalyst for various industrial processes, such as, for example, alkylation, isomerization, hydro-dehydrogenation processes, with an improved activity and selectivity with respect to the traditional amorphous silica-alumina gels.

24 Claims, No Drawings

CATALYTICALLY ACTIVE AMORPHOUS POROUS SOLID AND PROCESS FOR ITS PREPARATION

The present invention relates to a catalytically active amorphous porous solid and a process for its preparation.

More specifically, the present invention relates to an amorphous porous solid comprising a mixed oxide of silicon, aluminum and phosphorus, having porosity and acidity characteristics suitable for use as a catalyst or as an active carrier of a catalyst for a variety of acid-catalyzed industrial chemical processes.

Solid silica, alumina or silico-alumina compositions with an amorphous structure and having a catalytic activity in acid-catalyzed reactions, are known in the art. These compositions are generally characterized by a high porosity and surface area, and comprise sites with acid properties.

The patent EP 160,145, for example, describes an alkylation process of aromatic hydrocarbons in the presence of a catalyst based on amorphous silica and alumina (also commonly called silica alumina gel) with an average pore diameter ranging from 5 to 50 nanometers (nm) and with a silica/alumina molar ratio ($SiO_2/Al_2O_3$) ranging from 1/1 to 10/1.

U.S. Pat. Nos. 5,434,118 and 5,049,536 describe the preparation and use of amorphous compositions of silica and another metallic oxide, preferably alumina, having a porosity (pore volume) ranging from 0.4 to 0.8 ml/g, with a particularly narrow distribution of the pore diameter (average diameter between 2 and 4 nm) and a surface area higher than 500 $m^2/g$. These compositions are also used as catalysts for alkylation, oligomerization of primary olefins, cracking of hydrocarbons and in other typical acid-catalyzed reactions.

Other catalytic compositions based on amorphous silica and alumina are described in European patent applications EP-A 340,868, EP-A 659,478 and EP-A 812,804, characterized by a micro/mesoporous structure with a controlled pore size, having a surface area of at least 500 $m^2/g$, and with a molar ratio ($SiO_2/Al_2O_3$) ranging from 30/1 to 500/1, but preferably from 40/1 to 150/1. They are obtained by means of a process in which an aqueous solution of silicon and aluminum alkoxides is hydrolyzed and gelified by heating, either in a closed environment at boiling point or a higher value, or in an open environment below this temperature, in the presence of an ammonium compound for controlling the pH of the solution. The gel thus produced is subsequently subjected to drying and calcination. The final structure of the porous solid thus obtained critically depends on the gelification conditions and on the ammonium compound used, also defined in this case as templating agent.

These catalytic compositions are not only used as such, but also as active carrier of transition metals, especially of groups 8 to 10 of the periodic table of elements, for the formation of catalysts for hydrocracking reactions or the hydro-isomerization of hydrocarbons.

Catalytic compositions are also described, for various purposes, based on silico-aluminas with varying degrees of crystallinity, for example having the typical structure of zeolites or molecular sieves, which are used as catalysts in the above chemical processes. These crystalline or semicrystalline catalysts having a strong acidity, however, are not satisfactory in certain industrial processes, such as for example, hydrocracking processes to obtain medium distillates, as they tend to direct the cracking reaction towards the formation of low molecular weight products.

Different catalytic compositions based on silica and alumina, containing one or more other elements suitable for providing the end-product with particular characteristics, are also known in the art. Silico-aluminas are known for example, containing vanadium or titanium, suitable as catalysts in oligomerization reactions.

Wide literature is also available on molecular sieves based on silica and alumina additionally comprising a phosphorus compound (so-called SAPO®). U.S. Pat. No. 4,859,311, for example, describes molecular sieves consisting of silico-alumino-phosphates having a microporous structure with an average pore diameter ranging from 0.3 to 0.7 nm, on which one or more metals with a hydro-dehydrogenating activity, used for removing waxy components of certain paraffinic mixtures (catalytic dewaxing), are deposited. These compositions, however, do not seem to be entirely satisfactory as catalysts in integrated processes for the production of lubricating bases and medium distillates from high-boiling linear paraffinic fractions.

According to European patent EP 492,697, a catalytic composition is described, consisting of an amorphous porous solid comprising silica and at least one oxide of a second metal having a catalytic activity selected from Ti, Ga, Cr, Fe, Zr, V, Mo, Zn, Co, P and Sn. Although this matrix of oxides has various uses as acidic or oxidation catalyst, it does not contain aluminum and is consequently not satisfactory as an active carrier for the hydrogenating and isomerization treatment of paraffinic mixtures.

U.S. Pat. No. 5,230,789 describes certain particular catalytic compositions consisting of amorphous solid solutions containing from 5 to 50% by weight of alumina, from 10 to 90% by weight of silica and from 5 to 40% by weight of phosphate (as $P_2O_5$), which can be used as such or as carriers for metals with a catalytic activity in transformation processes of hydrocarbons such as those mentioned above, even if only their use in the production of medium distillates is illustrated. The method used for preparing these solid solutions comprises the formation of a gel of the relative Si and Al hydroxides containing the desired quantity of phosphate, starting from a sol acidified with hydrochloric acid. The solid solutions thus obtained however are not entirely satisfactory when used in integrated processes for the upgrading of paraffinic mixtures with the purpose of obtaining a wide range of products.

One of the major problems in the hydrocracking process of mixtures of linear paraffins consists in the difficulty in contemporaneously obtaining medium distillates with good low temperature properties and a 360+° C. fraction with suitable characteristics, in terms of average molecular weight and isomerization degree, for the production of bases for lubricating oils. If a 150+° C. cut is subjected to hydrocracking, with the catalytic systems currently in use, it can be observed that if the reaction is carried out so as to obtain medium distillates with good low temperature characteristics, the 360+° C. residue has a molecular weight which is too low and consequently the lubricating base obtained has a low viscosity. When the reaction, on the other hand, is carried out so as to obtain a 360+° C. cut with a sufficiently high average molecular weight, the yields to lubricating base are in any case low due to the presence of a quantity of linear paraffins which is still high, which necessitates a subsequent dewaxing step and, in addition, the low temperature characteristics of the medium distillates are not satisfactory.

No solution seemed as yet to have been found to the above overall problems with respect to the processes and catalysts of the known art. Even though the use, as catalyst carrier, of certain particular amorphous micro-meso-porous silico-aluminas, as described in European patent application EP-A 1,101,813, is capable of providing an excellent equilibrium between gas oil and kerosene in the medium distillate fraction, it apparently does not allow a fraction of lubricating base to be produced with optimal characteristics which enable it to be adopted without any further specific treatment.

It has now been surprisingly found that certain amorphous silico-aluminas with a low aluminum content, containing certain quantities of phosphorus, bound to the oxide matrix, surprisingly allow a catalytically active solid to be obtained, not described so far, having particularly advantageous characteristics, both when used as such in acid-catalyzed and oligomerization processes, and also as active catalyst carrier in refining processes such as the hydro-treatment of hydrocarbons for the production of fuels and bases for lubricating oils.

A first object of the present invention therefore relates to an amorphous porous solid, catalytically active, comprising a mixed oxide of silicon, aluminum and phosphorus, characterized by an Si/Al atomic ratio ranging from 10 to 250, a P/Al ratio of at least 0.1, but lower than 5, preferably ranging from 0.3 to 3.5, a total pore volume ranging from 0.5 to 2.0 ml/g, with an average pore diameter ranging from 3 nm to 40 nm, and a specific surface area ranging from 200 to 1000 m$^2$/g, preferably from 300 to 900 m$^2$/g.

A second object of the present invention relates to an original process for the preparation of said amorphous porous solid by means of the sol/gel technique starting from Si and Al alkoxides and at least one phosphorus compound suitable for the purpose.

Other objects of the present invention will appear evident from the following description and claims.

The term amorphous as used herein with reference to the porous solid of the present invention and its compositions and uses, indicates a substantial absence of low angle X-ray scattering signs, according to the usual measuring technique described further on.

In its most general form, the catalytically active solid according to the present invention essentially comprises an amorphous homogeneous phase of a mixed oxide of silicon, aluminum and phosphorus, wherein the phosphorus is in the maximum oxidation state (+5) and is prevalently bound to the matrix by means of P—O—Al bonds, as determined by means of $^{27}$AL-NMR and $^{31}$P-NMR spectroscopic analysis. It has an extremely high surface area (determined with the BET method), preferably ranging from 300 to 900 m$^2$/g, more preferably from 400 to 800 m$^2$/g, and a pore size within the range of mesopores, preferably with an average diameter (determined with the DFT method) ranging from 5 to 30 nm, more preferably from 6 to 25 nm. The porosity (total pore volume in ml/g) is extremely high and can be regulated, within certain limits, through the times, temperatures and other operating parameters during the preparation process of the gel. The porosity of the amorphous solid preferably ranges from 0.7 to 1.7 ml/g.

From a morphological point of view, the amorphous porous solid of the present invention comprises a non-ordered network of pores with an essentially monomodal size distribution within a relative wide range. The difference between 10% and 90% of the pore dimensions in the distribution curve is preferably within a range of diameters from 2 to 40 nm, preferably from 10 to 35 nm. The oxides forming the matrix are in turn arranged disorderly in a tridimensional polymeric lattice, without forming crystalline structures detectable with X-rays.

The amorphous porous solid according to the present invention prevalently consists of silicon oxide and is characterized by the presence of certain quantities of Al and P uniformly bound and distributed in the oxide matrix, so that the P/Al ratio is lower than 5 and at least equal to 0.1. For P/Al ratio values of 5 or higher, a substantial collapse of the porous structure is observed, with a considerable decrease in the catalytic and carrier properties; for P/Al values lower than 0.1, no substantial progress was observed with respect to a traditional amorphous silica and alumina matrix having an analogous composition more advantageous results were obtained when the P/Al ratio ranges from 0.3 to 3.5, and particularly within the range of 0.5 to 2.5.

One of the essential characteristics of the amorphous porous solid of the present invention is the selection of the aluminum content within a narrow and quantitatively limited range, which in turn determines the phosphorus content range. The Si/Al atomic ratio preferably ranges from 15 to 200, more preferably from 20 to 150.

The amorphous porous solid according to the present invention can also comprise, when necessary, smaller quantities of other components, in a mixture or dispersed in the oxide matrix, in particular other metallic compounds, especially oxides, suitable for giving particular characteristics or other desirable catalytic functions. According to a preferred aspect, said amorphous porous solid comprises at least 90% by weight, preferably 95%, of said mixed oxide of Si, Al and P, and up to 10% by weight, preferably up to 5% by weight of said additional components. In particular, the solid according to the present invention can contain in admixture oxides of phosphorus or phosphates not bound to the matrix of amorphous oxide of silicon, aluminum and phosphorus. Other oxides which can be present are those of certain transition metals, particularly selected from Ti, Zr, V, Cr, Fe, Co, Ni, Pt, Pd, Mo, Zn, Ga and Sn, whereas alkaline or alkaline earth metals are preferably absent or only present in traces. These metals can advantageously provide the amorphous solid of the present invention with improved mechanical properties and further catalytic functions, such as oxidation and hydro-dehydrogenation, which are requested for certain industrial processes.

The amorphous porous solid according to the present invention can be prepared by adapting various typical sol-gel methods for the preparation of micro- or meso-porous amorphous silico-alumina, by the addition of a suitable quantity of an appropriate phosphorus compound in any of the steps preceding calcination, preferably before or during the formation of the gel. The phosphorus compound is preferably selected form organic or inorganic oxygenated compounds, capable of forming phosphorus oxide or a phosphate group after the oxidizing thermal treatment suitable for drying and calcining the gel, more preferably such as to avoid introducing traces of undesirable metals in the matrix of porous oxide obtained after calcination.

Sol-gel methods for the preparation of amorphous silico-aluminas which can be adapted for the purpose are described, for example, in European patent applications EP-A 160,145, EP-A 340,868 and EP-A 659,478 or in the publication Journal of Catalysis, Vol. 60 (1969), pages 156-166, whose contents are incorporated herein as reference, without limiting the scope of the present invention to said methods.

An advantageous preparation method, which forms a second object of the present invention, includes, in a first step (i), the preparation of a mixture comprising a tetra-alkyl ammonium hydroxide, having the function of templating agent, an aluminum compound and a silicon compound, which can be hydrolyzed to the corresponding hydrated oxides, an oxygenated compound of phosphorus and a sufficient quantity of water to dissolve and hydrolyze said compounds, wherein said tetra-alkyl ammonium hydroxide comprises from 1 to 10 carbon atoms in each alkyl residue, said hydrolyzable aluminum compound is preferably an aluminum trialkoxide comprising from 1 to 10 carbon atoms in each alkoxide residue, said hydrolyzable silicon compound is a silicate of at least one hydrocarbon residue, preferably a tetra-alkylorthosilicate, comprising form 1 to 10 carbon atoms for each alkyl residue, and said oxygenated phosphorus compound is a salt or phosphate or phosphonic ester or the corresponding acid, preferably an ammonium salt or an ester of phosphoric, phosphorous or phosphonic acid, in which each alkyl residue comprises from 1 to 10 carbon atoms.

The aqueous mixture of the above compounds is then hydrolyzed and gelified in a second step (ii), by heating in an alkaline environment, preferably at a pH greater than 10, either by refluxing in a closed vessel, at the normal boiling point or higher, or in an open vessel below this temperature, so that there is essentially no exchange of material with the outside. The gel thus produced is subsequently subjected to a third drying and calcination step (iii).

The aqueous mixture in step (i) can be made up of water or a mixture of water and a soluble oxygenated organic compound, preferably an alcohol having from 1 to 10 carbon atoms, in a quantity of up to 1/1 in moles with respect to the water. More preferably, the oxygenated compound is an alcohol having from 2 to 5 carbon atoms. During the hydrolysis, a further quantity of alcohol is released in the aqueous solvent.

The tetra-alkyl ammonium hydroxide which can be used for the purposes of the present invention is selected for example from tetra-ethyl, propyl-, isopropyl-, butyl-, isobutyl-, terbutyl, and pentyl-ammonium hydroxide and among these tetra-propyl-, tetra-isopropyl- and tetra-butyl ammonium hydroxide are preferred. The aluminum trialkoxide is selected, for example, from aluminum triethoxide, propoxide, isopropoxide, butoxide, isobutoxide and terbutoxide and among these aluminum tripropoxide and triisopropoxide are preferred. The tetra-alkyl orthosilicate is selected for example from tetra-methyl-, tetra-ethyl-, propyl-, isopropyl-, butyl-, isobutyl-, terbutyl-, and pentyl-orthosilicate and among these tetra-ethyl orthosilicate is preferred.

The oxygenated phosphorus compound is preferably selected from organic or inorganic compounds soluble in the reaction mixture of step (i), comprising a phosphate, phosphite or phosphonic group. According to an applicative aspect of the present invention, the phosphorus compound can also be formed in situ in the reaction mixture, or it can be added to said mixture in the form of a solution in a suitable solvent, preferably an alcohol or water. Typical phosphorus compounds suitable for the purpose are, for example, phosphoric acid, phosphorous acid, ammonium phosphate, quaternary ammonium phosphates with organic amines having from 1 to 5 carbon atoms for each residue bound to the nitrogen atom, organic phosphites and phosphates of alcohols having from 1 to 10, preferably from 1 to 5 carbon atoms, acid phosphates of ammonium or quaternary ammonium, alkyl-phosphonates or alkyl-phosphinates of alkyl residues having from 1 to 10, preferably from 1 to 5, carbon atoms. Particularly preferred phosphorus compounds are ammonium phosphate, acid ammonium phosphate and the corresponding quaternary phosphates with organic amines having from 1 to 4 carbon atoms per residue, especially in the form of a solution prepared by the addition in water of phosphoric acid and the corresponding stoichiometric quantity of ammonia or amine.

In the preparation of the mixture of step (i), the order of addition of the various reagents is not particularly critical. The phosphorus compound can be added or formed in situ initially, together with the addition of the tetra-alkylammonium hydroxide, by regulating the quantities so as to respect the desired final ratios between atoms and components, or it can be added after the introduction of the Si and Al compounds. The mixture is prepared at room temperature or a slightly higher value, preferably between 30 and 80° C. Although the mixture of step (i) preferably consists of a limpid solution, certain compounds, such as aluminum alkoxide for example, can remain partially undissolved, but are completely dissolved in the heating phase and hydrolysis of the subsequent step (ii). In certain cases, a time of up to five hours under stirring may be necessary for obtaining a solution.

In a preferred embodiment of the process for the preparation of the amorphous solid according to the present invention, an aqueous solution is first prepared, containing the phosphorus compound, the tetra-alkyl ammonium hydroxide and the aluminum trialkoxide, operating at a temperature which is sufficient to guarantee an effective dissolution of the aluminum compound, preferably from 40 to 80° C. The tetra-alkyl orthosilicate is added to said aqueous solution. If necessary, the pH is regulated to a value greater than 10, preferably between 11 and 12, usually by the addition of a suitable alkaline compound, preferably the same ammonium salt used as templating agent. The mixture is brought to a temperature which is suitable for triggering the hydrolysis reaction. Said temperature is in relation to the composition of the reaction mixture (normally from 60 to 120° C.). The hydrolysis reaction is exothermic and therefore guarantees self-maintenance, once the reaction has been activated. The quantities of constituents of the mixture are selected so as to respect the atomic ratios between the elements to be obtained in the amorphous porous solid at the end of the preparation; the following atomic or molar ratios are conveniently used: Si/Al from 10/1 to 250/1, tetra-alkyl ammonium hydroxide/Si from 0.05/1 to 0.2/1, $H_2O$/Si from 5/1 to 40/1, P/Al from 0.1 to 5.0. The preferred values for these ratios are: Si/Al from 20/1 to 150/1, tetra-alkyl ammonium hydroxide/Si from 0.05/1 to 0.2/1, P/Al from 0.5 to 3. 5 and $H_2O$/Si from 10/1 to 25/1.

The hydrolysis of the reagents and their gelification are preferably effected operating at a temperature equal to or higher than the boiling point, at atmospheric pressure, of any alcohol which develops as by-product of said hydrolysis reaction, without eliminating or substantially eliminating said alcohols from the reaction environment. The hydrolysis and gelification temperature is therefore critical, and is conveniently maintained at values higher than about 65° C. up to about 110° C. Furthermore, in order to maintain the development of alcohol in the reaction environment, it is possible to operate in an autoclave at the autogenous pressure of the system at the pre-selected temperature (normally in the order of 0.11-0.15 MPa absolute), or at atmospheric pressure in a reactor equipped with a reflux condenser.

According to a particular embodiment of the process, the hydrolysis and gelification are carried out in the presence of a quantity of alcohol higher than that which develops as by-product. For this purpose, a free alcohol, advantageously having from 1 to 10 carbon atoms and preferably ethanol, is added to the reaction mixture in a quantity up to a maximum molar ratio between alcohol added and Si of 8/1.

The times necessary for completing the hydrolysis and gelification, under the conditions indicated above, usually vary from 10 minutes to 3 hours and are preferably in the order of 1-2 hours.

It has also been found useful to subject the gel thus formed to aging, by maintaining the reaction mixture in the presence of alcohol and under room temperature conditions for a period in the order of 1-24 hours.

The alcohol is finally removed from the gel which is dried, operating according to the known art, so as to avoid fracturing of the solid and substantially maintaining the pore structure unaltered. Reduced pressure is normally applied, generally from 1 to 20 kPa and preferably from 3 to 6 kPa, together with a temperature ranging from 50 to 120° C., preferably from 100 to 110° C. According to a preferred method, the drying is effected operating with a gradient (or profile) of (increasing) temperatures and (decreasing) pressures within the above ranges to allow the gradual evaporation of the solvent. The dried gel is finally subjected to calcination in an oxidizing atmosphere (normally in air), at a temperature ranging from 500 to 700° C. for a period of 4-20 hours and preferably from 500-600° C. for 6-10 hours, also in this case preferably operating with a suitable temperature gradient.

The gel based on silicon, aluminum and phosphorus hydrated oxides thus obtained has a composition corresponding to that of the reagents used, considering that the reaction yields are practically complete. The Si/Al molar ratio consequently varies from 10/1 to 250/1, preferably from 15/1 to 200/1, the most preferred values ranging from 20/1 to 150/1 and specifically in the order of 100/1. This gel is amorphous, when subjected to analysis by means of powder X-ray diffractometry, it has a surface area of at least 200 m$^2$/g and normally within the range of 300-800 m$^2$/g and a pore volume of 0.7-1.7 cm$^3$/g.

According to what is known in the art with respect to heterogeneous catalysis, the above catalytically active amorphous solid can be advantageously mixed and processes with other inert compounds such as, for example, pseudo-bohemite which for calcination becomes γ-alumina, suitable for providing enhanced mechanical and morphological properties, desirable for industrial use. Consequently, in accordance with a particular aspect of the present invention, said amorphous solid can, if necessary, form a catalytically active composition mixed with a suitable quantity of a binder consisting of an inert inorganic solid, generally added for the purpose of improving the mechanical properties, such as for example, silica, alumina, clay, titanium oxide ($TiO_2$) or zirconium oxide ($ZrO_2$), boron oxide ($B_2O_3$) or mixtures of these. It is generally preferably, in fact, for its industrial applications, for said solid to be used in granular rather than powder form, and for it to have a relatively narrow particle-size distribution. Furthermore, it is preferably endowed with sufficient mechanical resistance to compression and impact to avoid its progressive breakage during use, due to the fluid-dynamic and vibrational stress effected by the process fluids.

Possible binders can be all those which are known to be suitable for the purpose, both natural and synthetic, preferably silica and alumina, and particularly alumina in all its known forms, for example gamma-alumina.

Said catalytically active composition according to the present invention can be obtained by means of any of the mixing, extrusion and granulation (palletizing) methods of solid materials in a mixture, for example, according to the methods described in European patent applications EP-A 550,922 and EP-A 665,055, the latter preferred, both filed by the Applicant, whose contents are incorporated herein as reference.

In particular, according to a preferred method, the gel obtained from the hydrolysis and gelification of the aqueous mixture of Al alkoxide, tetra-alkyl silicate and oxygenated phosphorus compound, prepared as described above, is mixed, before the calcination step (iii), with the desired quantity of inorganic binder, based on the dry weight, normally with a weight ratio between binder and gel (humid) within the range of 0.05 to 0.5. A plasticizing agent, selected from those generally known to be suitable for the purpose is also preferably added, for example methyl cellulose, stearine, glycerol, more preferably methyl cellulose, to favour the formation of a homogeneous and easily processable paste. This plasticizer is generally added in a quantity ranging from 5 to 20 g per 100 g of binder.

A suitable acidifying compound selected from organic acids, such as acetic acid or acetic anhydride, oxalic acid, or inorganic acids, such as hydrochloric acid or phosphoric acid, is then added in a quantity preferably ranging from 0.5 to 8 g per 100 g of binder. Acetic acid is particularly preferred.

The mixture thus obtained is homogenized by mixing and heating to a temperature ranging from 40 to 90° C., with partial evaporation of the solvent, until a paste is obtained, and then extruded using suitable equipment. The extruded product is cut into cylindrical granules, preferably with a size of 2-100 mm in length and 0.5-4.0 mm in diameter. According to an alternative embodiment, the above homogeneous paste can also be dried in a suitable granulator, in order to obtain granules having the desired dimensions.

The granules thus obtained are subjected to progressive heating to eliminate the residual quantities of solvent and finally calcined-in an oxidizing atmosphere, generally in a stream of air, at a temperature ranging from 400 to 600° C., for 4-20, preferably 6-12 hours.

A composition is thus obtained in the form of a granular acid solid having the desired catalytic and mechanical properties, containing a quantity of 1 to 70% by weight, preferably from 20 to 50% by weight, of said inert inorganic binder, the remaining percentage consisting of the catalytically active amorphous solid according to the present invention. The granular solid is preferably in the form of pellets having a size of about 2-5 mm in diameter and 2-10 mm in length.

Both the porosity and surface area of the extruded product normally have average values with respect to the values of the single components in the mixture, according to linear composition rules.

The catalytically active amorphous solid of the present invention, both as such and mixed with other inert materials, has acidic characteristics. It is distinguished by the advantageous combination of a pore diameter and surface area which are both relatively high. According to the studies carried out by the Owner, this combination favours a particularly desirable catalysis selectivity and orientation, especially in hydrotreatment processes of hydrocarbons, and paraffins in particular. Said solid can therefore be used as catalyst or active carrier of a catalyst for various acid-catalyzed industrial processes such as, for example, alkylation, isomerization, oligomerization processes. It can also be advantageously used as active carrier in hydro-dehydrogenation reactions, for example in transformation processes of hydrocarbon fractions such as hydrocracking, hydro-isomerization and dewaxing, with improved activities and selectivities with respect to the traditional amorphous silica-alumina gel, particularly when a range of products from kerosene to lubricating bases is desired, thus reducing the use of dewaxing steps, separate or following the hydrocracking step, as much as possible.

In particular, for the preparation of a catalyst for hydrocracking and/or hydro-isomerization, a metal having a hydro-dehydrogenating activity when in the presence of hydrogen/hydrocarbon mixtures, is supported on the catalytically active porous solid according to the present invention. Metals especially suitable for the purpose are those of groups 6 to 10 of the periodic table, such as, for example, chromium, iron, cobalt, nickel, ruthenium, rhodium, palladium, iridium, osmium and platinum. Combinations of nickel with molybdenum, tungsten and cobalt as well as the noble metals platinum or palladium, and preferably platinum, are of particular interest.

According to the present invention, the metal should be conveniently distributed as uniformly as possible on the porous surface of the carrier, in order to maximize the catalytically surface which is effectively active. For this purpose, various known methods can be used, such as those described for example in European patent application EP-A 582,347, whose contents are incorporated herein as reference. In particular, according to the impregnation method, the amorphous porous solid of the present invention, as such or preferably extruded, is put in contact with an aqueous or alcoholic solution of a compound of the desired metal for a period sufficient to provide a homogeneous distribution of the metal in the solid. This normally requires from a few minutes to several hours, preferably under stirring. Soluble salts suitable for the purpose are, for example, $H_2PtF_6$, $H_2PtCl_6$, $[Pt(NH_3)_4]Cl_2$, $[Pt(NH_3)_4](OH)_2$ and analogous salts of palladium; mixtures of salts also of different metals are equally included in the scope of the invention. The minimum quantity of aqueous liquid (normally water or an aqueous mixture with a second inert liquid or with an acid in a quantity lower than 50% by weight) is conveniently used, which is sufficient to dissolve the salt and uniformly impregnate said carrier, preferably with a weight ratio solution/solid ranging from 1 to 3. The quantity of metal is selected on the basis of its concentration which is to be obtained in the catalyst, as the whole metal is fixed on the carrier.

At the end of the impregnation, the solution is evaporated and the solid obtained is dried and calcined in an inert or reducing atmosphere, under analogous temperature and time conditions as those cited above for the calcination of the amorphous solid or extruded product.

An alternative to the impregnation method is by ion exchange. According to the latter, the amorphous silica/alumina/phosphate solid is put in contact with an aqueous solution of a salt of the metal as in the previous case, but the deposition takes place by exchange under conditions made basic (pH between 8.5 and 11) by the addition of a sufficient quantity of an alkaline compound, normally an ammonium hydroxide. The suspended solid is then separated from the liquid by means of filtration or decanting and dried and calcined as specified above.

According to another alternative, the salt of the transition metal can be included in the catalytically active solid in the gel preparation step, for example before hydrolysis for the formation of a humid gel, or before its calcination.

A typical method for the preparation of a catalyst by the hydrotreatment of hydrocarbons comprising as carrier the active composition of the present invention, includes the following steps:

(a) solution A is prepared of the hydrolyzable components and ammonium phosphate as described above, in suitable quantities for obtaining the desired end-composition;

(b) the above solution is heated to 60-70° C. to cause its hydrolysis and gelification and to obtain a mixture B with a viscosity ranging from 0.01 to 100 Pa·sec;

(c) a binder, belonging to the group of bohemites or pseudobohemites, is first added to the mixture B, in a weight ratio with the mixture B ranging from 0.05 to 0.5, followed by methyl cellulose as plasticizer in a quantity ranging from 10 to 20 g per 100 g of binder; and finally a mineral or organic acid in a quantity ranging from 0.5 to 8.0 g per 100 g of binder;

(d) heating the mixture obtained under point (c) under mixing to a temperature ranging from 400 to 90° C. until a homogeneous paste is obtained, which is subjected to extrusion and granulation;

(e) the extruded product is dried and calcined in an oxidizing atmosphere.

In this way, a catalytically active granular composition is obtained, with acid characteristics, containing a quantity ranging from 30 to 70% by weight of inert inorganic binder, the remainder consisting of the active porous solid of silicon/aluminum/phosphorus oxide, of which the surface extension and structure are described above for the same porous solid without the binder. The granules are conveniently in the form of pellets having a size of about 2-5 mm in diameter and 2-10 mm in length.

The supporting step of the noble metal on the active granular solid is effected with the same procedure specified above.

Before use, the catalyst thus obtained is normally subjected to activation in a reducing atmosphere, according to one of the known methods suitable for the purpose, which can also be carried out directly in the reactor preselected for the hydrocracking reaction. A typical method uses the procedure described hereunder:

1) 2 hours at room temperature in a steam of nitrogen;
2) 2 hours at 50° C. in a stream of hydrogen;
3) heating to 310-360° C. with an increase of 3° C./min in a stream of hydrogen;
4) constant temperature of 310-360° C. for 3 hours in a stream of hydrogen and cooling to 200° C.

During the activation, the pressure in the reactor is maintained between 3.0 and 8.1 MPa (30 to 80 atms).

Some examples of practical embodiments are provided for a more detailed description of the present invention, which however are purely illustrative of some of the particular aspects of the invention and should in no way be considered as limiting its overall protection scope.

EXAMPLES

The following analysis and characterization methods were used for effecting the practical embodiments of the present invention:

X-ray diffractometry from powders (XRD): the analysis was carried out using a vertical Philips X'PERT diffractometer equipped with a proportional pulsating meter and a secondary curved graphite crystal monochromator; two different tests were effected for each sample: the first of the angular region $1.5 \leq 2\theta \leq 10°$ with a step of $0.05°$ $2\theta$ and accumulation times of 20s/step and fixed divergent slips of 1/6°; the second within the spectral range of $3 \leq 2\theta \leq 53°$ with a step of $0.05°$ $2\theta$ and accumulation times of 10 s/step and fixed divergent slips of 1°;

in both cases the radiation was CuKα ($\lambda=1.54178$ Å).

The total specific pore volume ($V_P$) was calculated using the Gurvitsch method at $p/p°=0.995$. The adsorption/desorption isotherms of $N_2$ at the temperature of liquid $N_2$, were obtained using an ASAP 2010 instrument (Micrometrics) and a Sorptomatic 1990 (ex Carlo Erba). Before acquiring the isotherms, the samples (~0.3 g) were degassed for 16 hours at 350° C. at reduced pressure.

The average pore diameter was determined by means of the DFT (density functional theory) method, of which details are provided in the publication of P. A. Webb and C. Orr, in "Analytical Methods in Fine Particle Technology", Micrometrics Instruments Corp. (1997), page 81.

The specific surface area was evaluated by means of the BET linear graph with two parameters within the range of p/p° 0.01-0.2 applying the DFT (density functional theory) method.

Pour point: according to the standard method ASTM D97

Viscosity @100° C.: according to the standard method ASTM D445

Viscosity index: according to the standard method ASTM D2270

Reagents and Materials

The commercial reagents listed below were used during the preparations described in the examples:

| | |
|---|---|
| tetrapropylammonium hydroxide (TPA-OH) | SACHEM |
| aluminum tri-isopropoxide | FLUKA |
| tetra-ethylsilicate | DYNAMIT NOBEL |
| alumina (VERBAL 250, Pseudo-Boehmite) | LAROCHE |
| methyl cellulose (METHOCEL) | FLUKA |
| phosphoric acid | CARLO ERBA |

The reagents and/or solvents used and not indicated above are those most commonly used and can be easily found at the normal commercial suppliers specialized in the field.

Example 1

Porous Solid with P/Al=1

239.50 ml of demineralized water, 3.40 g of an ammonia solution at 30% by weight and 2.30 g of a solution of phosphoric acid at 85% by weight (equivalents at 0.02 moles of tri-ammonium phosphate $(NH_3)_3PO_4$), are charged into a three-necked flask, equipped with a rod stirrer and a bubble cooler. 50.80 g of an aqueous solution at 40% by weight of tetrapropylammonium hydroxide (TPA-OH, 0.01 moles) and 4.08 g of aluminum tri-isopropoxide (0.02 moles) are added to the mixture thus prepared. The mixture is maintained under stirring at room temperature for about 60 minutes, until a limpid solution is obtained. 208 g of tetra-ethylorthosilicate (TEOS; 1.00 moles) are rapidly added to this solution and the temperature is brought to 60° C., the whole mixture being maintained under stirring under these conditions for a further 3 hours. At the end the formation of a gel is observed, which is cooled to room temperature and left to rest for 20 hours. In this way a homogeneous gel is obtained, characterized by the following molar ratios between the constituents: Si/Al=51; TPA-OH/Si=0.098; $H_2O$/Si=15; Si/P=50.

The gel thus obtained is first dried in air for about 3 hours and then calcined by heating, still in a stream of air, at 550° C. for 5 hours. At the end, an amorphous solid is obtained according to the present invention, identified by the following empirical formula: $SiAl_{0.02}P_{0.02}O_{2.08}$.

The complete absence of crystalline aggregates was confirmed by means of X-ray diffraction. By means of NMR spectroscopy applied to the $^{31}P$ and $^{27}Al$ isotopes, it was found that at least 80% of the phosphorus is bound by Al—O—P bonds to the amorphous silico-alumina matrix. The results of the morphological analysis are summarized in Table 1 below.

Examples 2 and 3

The procedure according to the previous example 1 was repeated modifying each time the quantity of tri-ammonium phosphate initially produced by mixing ammonia and phosphoric acid in aqueous solution, so that the P/Al ratio in the gel ranges from 0.5 to 2 for Examples 2 and 3 respectively.

The structure of the solid catalysts thus obtained, determined by means of X-ray diffraction and NMR spectroscopy showed that they were completely amorphous solid in which at least 80% of the phosphorus is bound by means of Al—O—P bonds to the silico-alumina matrix, analogously to the product according to Example 1.

The results of the morphological analysis and elemental analysis are summarized in Table 1 below.

Example 4

The procedure of Example 1 was repeated exactly, with the only difference that the hydrolysis and gelification step is carried out in an ethanol/water mixture in which the molar ratios ethanol/$SiO_2$=8 and $H_2O$/$SiO_2$=8. At the end the product thus obtained is subjected to characterization according to the above techniques. The morphological data are indicated in Table 1 below.

Example 5 (Comparative)

The procedure of Example 1 was repeated exactly, with the only difference that the P/Al ratio in the gel was equal to 5, instead of 1.

The structure of the solid thus obtained, determined by means of X-ray diffraction and NMR spectroscopy, proved to be analogous to that of the product of Example 1, but the pore structure was greatly modified, with a partial collapse, as shown by the significant reduction in their volume.

Example 6 (Comparative)

An amorphous silica-alumina solid carrier was prepared not containing phosphorus, repeating the same procedure as the previous Example 1, but without introducing the solution of tri-ammonium phosphate. The results of the characterization are summarized in Table 1 below. A significant reduction in the average pore diameter is observed.

TABLE 1

Morphological properties of the catalysts

| Example | Si/Al | P/Al | $S_{BET}$ (m²/g) | Vp (ml/g) | $d_{DFT}$ (nm) |
|---|---|---|---|---|---|
| 1 | 50 | 1.0 | 700 | 0.96 | 6.1 |
| 2 | 50 | 0.5 | 720 | 0.84 | 5.3 |
| 3 | 50 | 2.0 | 520 | 1.62 | 25.0 |
| 4 | 50 | 2.0 | 760 | 1.57 | 13.0 |
| 5 (comp.) | 50 | 5 | 80 | 0.06 | — |
| 6 (comp.) | 50 | 0 | 760 | 0.49 | 2.3 |

Example 7

Extruded Catalyst 5 kg of a humid gel prepared by exactly repeating the procedure of the previous Example 1, but omitting the drying and calcination phase, 1.466 kg of alumina (pseudobohemite, VERSAL 150), previously dried for 3 hours in air at 150° C., and 0.205 kg of methyl cellulose are charged into a 10 litre plough mixer, maintained at a stirring rate of 70-80 revs per minute, and the mixture is left under stirring for about 1 hour. 50 ml of glacial acetic acid are then added and the temperature of the mixer is brought to about 60° C., continuing the stirring until a homogeneous paste is obtained, having the desired consistency for the subsequent extrusion. The mixture is charged into an extruder of the HUTT type, extruded and cut into cylindrical granules (pellets) of the desired size (about 2×4 mm). The product is left to rest for about 6-8 hours and then dried by maintaining it in a stream of air at 100° C. for 5 hours. It is finally calcined in a muffle at 550° C. for 5 hours in a stream of air.

A porous extruded solid is thus obtained, with acidic characteristics (indicated hereunder with the term "extruded product" for the sake of simplicity), essentially consisting of an amorphous silica/alumina/phosphate phase (60% by weight, by means of X-ray diffraction) and an alumina crystalline phase (pseudo-bohemite), whose morphological characteristics are specified in Table 2 below.

Examples 8, 9 and 10 (Comparative)

The same procedure was repeated as the previous Example 7, but substituting the amorphous solid prepared according to Example 1 with the solids prepared according to the respective examples as indicated in the second column of Table 2 below.

Porous extruded solids are thus obtained, whose morphological characteristics are specified in Table 2.

TABLE 2

Morphological properties of the extruded products

| Example | Amorphous phase (Example Nr.) | P/Al | $S_{BET}$ (m$^2$/g) | Vp (ml/g) | $d_{DFT}$ (nm) |
|---|---|---|---|---|---|
| 7 | 1 | 1 | 540 | 0.91 | 7.6 |
| 8 | 3 | 2 | 460 | 1.26 | 18.0 |
| 9 | 4 | 2 | 510 | 1.25 | 16.0 |
| 10 (comp) | 6 | 0 | 590 | 0.88 | <6.0 |

Example 11

Formation of a Hydrocracking Catalyst Based on Platinum

In order to demonstrate the advantageous properties of the amorphous solid of the present invention as a catalytically active carrier in hydro-treatment processes of hydrocarbons, a hydrocracking catalyst was prepared, containing platinum as hydro-dehydrogenation metal.

In order to disperse the platinum on the carrier an aqueous solution of hexachloroplatinic acid ($H_2PtCl_6$), hydrochloric acid and acetic acid was used in the following molar ratios: $H_2PtCl_6/HCl/CH_3COOH=1/0.84/0.05$, having a concentration of platinum of $7.69 \cdot 10^{-3}$ M. 60 ml of this solution were added to 30 g of the extruded solid, obtained according to the previous Example 7, so that the whole solid was covered by the solution, in order to avoid heterogeneity in the platinum distribution. The suspension thus obtained was maintained under stirring for about an hour and then degassed by suction under vacuum (about 1 kPa) at room temperature. The solvent was subsequently removed by heating to about 70° C. in a stream of air. The dry product was finally calcined in a stream of air with the following temperature profile 25-350° C. in 2 hours, to 350° C. for 2 hours, 350-400° C. in 50 min., to 400° C. for 3 hours.

At the end, a supported catalyst for hydrocracking is obtained, having the following characteristics:

59.8% by weight of active amorphous solid (molar ratio Si/Al=51, P/Al=1)

39.9% by weight of gamma-alumina 0.3% by weight of platinum

Examples 12, 13 and 14 (Comparative)

A further three samples of hydrocracking catalyst were prepared, exactly repeating the procedure of the previous Example 11, but using the extruded products according to Examples 8, 9 and 10, in Examples 12, 13 and 14 (comparative) respectively. The composition characteristics relating to amorphous phase, gamma-alumina and platinum content of the catalysts obtained are essentially the same as Example 11, whereas the morphological measurements are specified in Table 3 below.

TABLE 3 morphological characteristics of the catalysts

| Example | P/Al | $S_{BET}$ (m$^2$/g) | Vp (ml/g) | $d_{DFT}$ (nm) |
|---|---|---|---|---|
| 11 | 1 | 490 | 0.84 | 7.3 |
| 12 | 2 | 430 | 1.12 | 15.0 |
| 13 | 2 | 470 | 1.02 | 16.0 |
| 14 (comp) | 0 | 510 | 0.82 | n.d. |

Example 15

120 ml of the aqueous solution of hexachloroplatinic acid used in the previous examples ($H_2PtCl_6/HCl/CH_3COOH=1/0.84/0.05$, [Pt]=$7.69 \cdot 10^{-3}$ M, were added to 30 g of the extruded solid obtained according to the previous Example 8, so that the whole solid is covered by the solution, in order to avoid heterogeneity in the platinum distribution. The suspension thus obtained was treated with the same procedure described in the previous Example 11, to obtain at the end, after calcination, a supported catalyst for hydrocracking, having the following characteristics:

59.8% by weight of active amorphous solid (molar ratio Si/Al=51, P/Al=1)

39.9% by weight of gamma-alumina 0.59% by weight of platinum

Examples 16 to 20

Catalytic Activity Tests in the Hydrocracking Reaction of Paraffinic Waxes

In order to verify the advantages of the catalytically active solid of the present invention when used as active carrier, various hydrocracking tests were carried out on a mixture of paraffins with a melting point higher than room temperature, using the catalysts of the previous Examples 11 to 15.

The hydrocracking tests were effected in a fixed bed tubular reactor having a useful charge volume of 15 ml, corresponding to a height of the catalytic bed in the isotherm section of about 10 cm. The reactor is equipped with suitable connections for the continuous feeding of the reagents in equicurrent and the removal of the reaction mixture. Hydrogen is fed at the desired pressure by means of a mass flow meter; the mixture of paraffins is maintained in the liquid state at a temperature of about 110° C. and fed by means of a pump.

The temperature of the reactor is controlled by means of a thermostat system capable of operating at up to 400° C. An adequate analytical instrumentation is connected on line for analysis in real time of the composition of the reaction product.

8 g of catalyst are charged into the reactor and activated according to the method described above.

A mixture of paraffins is used as feeding, obtained by mixing pure linear paraffins or mixtures with a very narrow distribution, having the following composition:

| | |
|---|---|
| Fraction < 150° C. | absent |
| Kerosene (from 150 to 260° C.) | 29.0 |
| Gas oil (from 260 to 370° C.) | 25.7 |
| Fraction > 370° C. | 45.3 |

Various hydrocracking tests were carried out on said paraffinic composition, at a total pressure of about 5 MPa and a weight ratio hydrogen/(hydrocarbon mixture) of about 0.1. Table 4 below indicates the experimental conditions and catalysts used in Examples 15 to 18. The contact time (1/WHSV) was regulated according to the usual technique in order to have the desired conversion degrees at the end.

TABLE 4

| | Process conditions | | | | |
|---|---|---|---|---|---|
| Conditions | Ex. 16 | Ex. 17 | Ex. 18 | Ex. 19 | Ex. 20 (*) |
| Temperature (° C.) | 335 | 340 | 333 | 340 | 353 |
| $H_2$/waxes (w/w) | 0.10 | 0.13 | 0.113 | 0.11 | 012 |
| Pressure (MPa) | 5.0 | 5.0 | 5.0 | 4.75 | 4.75 |
| Catalyst (Ex. Nr) | Ex. 11 | Ex. 12 | Ex. 13 | Ex. 15 | Ex. 14 (comp) |
| P/Al | 1 | 2 | 2 | 2 | 0 |
| WHSV ($h^{-1}$) | 1 | 1.5 | 3 | 1.5 | 2 |

(*) comparative

A fractionation was effected on the outgoing mixture by means of gas-chromatographic analysis, and on this basis, the conversion degree is measured of the hydrocarbon fraction having more than 22 carbon atoms $C_{22}+$, corresponding more or less to the fraction with a boiling point >370° C. Table 5 below indicates the composition data relating to the yields in the various distillation cuts obtained at the end of the process.

The residue with a boiling point higher than 360° C. is separated from a part of the above outgoing mixture, to be used as lubricating base, following bland dewaxing treatment to eliminate the residual traces of linear hydrocarbons. For this purpose, this 360+ residue is dissolved at 40° C. in a 1/1 vol/vol mixture of methyl-ethylketone and toluene. The (solvent)/(360+residue) ratio is 4/1 vol/vol; a part of the solvent (about ⅛ of the total) is used in the washing phase of the paraffin collected on the filter. The temperature of the solution is lowered to −20° C. at a rate of 1° C./min. At the end, the mixture is filtered at a temperature of −20° C. The dewaxed product is separated from the solvent by distillation under vacuum and subsequent stripping in a stream of nitrogen at 80° C. The quantity of product obtained, is measured to determine the content of lubricating base of said 360+ residue (Table 5). The lubricating base is then characterized by measuring the viscosity @100° C. and viscosity index. The results are indicated in Table 5 below, which clearly demonstrates the surprising improvements obtained with the catalytically active carrier of the present invention, with respect to a silica-alumina carrier having an analogous composition but not containing phosphorus. In particular, according to Examples 16 to 19 according to the present invention, it is possible to obtain, by means of a single hydrocracking step, a high yield to medium distillates (columns 150-260 and 260-370) and a high-boiling residue containing over 80% by weight of lubricating base having a much higher viscosity than that obtained under the same process conditions with a catalyst of the known art (comparative Example 20).

In addition to what is described above, other possible embodiments or equivalent modifications of the present invention not specifically mentioned herein, should be considered as being simple variations thereof which are in any case included in the scope of the following claims.

TABLE 5

Composition and properties of the hydrocracking product.

| Ex. | Temp. (° C.) | WHSV ($h^{-1}$) | Convers $C_{22}+$ | Yields to hydrocracking products (w %) (distillation ranges of fractions in ° C.) | | | | Yield % of 360+ residue | Lubricating base | |
|---|---|---|---|---|---|---|---|---|---|---|
| | | | | <150 | 150-260 | 260-370 | >370 | | Viscosity @100° C. (cSt) | Viscosity index |
| 16 | 335 | 1 | 78.7 | 7.2 | 42.5 | 40.7 | 9.6 | 89 | 4.33 | 147 |
| 17 | 340 | 1.5 | 72.3 | 6.6 | 40.8 | 40.1 | 12.5 | 88 | 4.47 | 135 |
| 18 | 338 | 1.5 | 74.5 | 7.6 | 43.7 | 37.2 | 11.5 | 92 | 4.31 | 145 |
| 19 | 333 | 3 | 79.0 | 10.8 | 43.5 | 36.2 | 9.5 | 84 | 4.27 | 142 |
| 20(*) | 352 | 2 | 83 | 9.3 | 40.5 | 42.5 | 7.7 | 91 | 2.73 | 143 |

(*) Comparative

The invention claimed is:

1. A catalytically active amorphous porous solid, comprising:
   a mixed oxide of silicon, aluminum, and phosphorous, wherein the mixed oxide has
   an atomic ratio Si/Al ranging from 20 to 250,
   an atomic P/Al of at least 0.1 and not higher than 3.5,
   a total pore volume ranging from 0.5 to 2.0 ml/g, with an average diameter ranging from 3 to 40 nm, and
   a specific surface area ranging from 200 to 1000 $m^2$/g.

2. The solid according to claim 1, wherein, in the mixed oxide, said atomic ratio Si/Al ranges from 20 to 200 and said atomic ratio P/Al ranges from 0.3 to 3.5.

3. The solid according to claim 1, wherein
said pore volume ranges from 0.7 to 1.7 ml/g, with an average diameter ranging from 5 to 30 nm, and
said surface area ranges from 300 to 900 $m^2/g$.

4. The solid according to claim 1, wherein the difference between 10% and 90% of the pore dimensions in the distribution curve is within a diameter range of 2 to 40 nm.

5. The solid according to claim 1, comprising at least 95% by weight of said mixed oxide and up to 5% by weight of at least one oxide of a metal selected from the group consisting of Ti, Zr, V, Cr, Fe, Co, Ni, Pt, Pd, Mo, Zn, Ga, and Sn.

6. A catalytically active solid composition comprising
from 30 to 99% by weight of the amorphous porous solid according to claim 1, and
from 70 to 1% by weight of an inert inorganic binder.

7. The composition according to claim 6, comprising
from 50 to 80% by weight of said amorphous porous solid and
from 50 to 20% by weight of said inert inorganic binder.

8. The composition according to claim 6, wherein said inert binder is selected from silica, alumina, clay, titanium oxide ($TiO_2$), zirconium oxide ($ZrO_2$), boron oxide ($B_2O_3$), or mixtures thereof.

9. The composition according to claim 6, wherein said inert binder essentially consists of alumina.

10. The composition according to claim 6, having the form of pellets with a diameter of 2 to 5 mm and a length of 2 to 10 mm.

11. A method of using a catalytically active amorphous porous solid, the method comprising contacting the solid of claim 1 with hydrocarbons in an alkylation process, an isomerization process or an oligomerization process.

12. A process for the preparation of a porous solid according to claim 1, comprising the following in succession:
(i) preparing an aqueous mixture comprising a tetra-alkyl ammonium hydroxide, a hydrolyzable aluminum compound, a hydrolyzable silicon compound and an oxygenated compound of phosphorus in such proportions as to have an atomic ratio Si/Al ranging from 20 to 250 and an atomic ratio P/Al ranging from 0.1 to 3.5, and a sufficient quantity of water to dissolve and hydrolyze said compounds;
(ii) heating said mixture in an alkaline environment, so that there is essentially no exchange of material with the outside, to obtain the formation of a gel; and
(iii) drying and calcinating the gel of (ii) to obtain the desired amorphous porous solid.

13. The process according to claim 12, wherein
said aluminum compound is an aluminum trialkoxide comprising from 1 to 10 carbon atoms in each alkoxide residue,
said hydrolyzable silicon compound is a silicate of at least one hydrocarbon residue, comprising from 1 to 10 carbon atoms for each alkyl residue, and
said oxygenated compound of phosphorus is a phosphoric or a phosphonic salt, or an ester, or a corresponding acid.

14. The process according to claim 13, herein said phosphorus compound is an ammonium salt or an ester of the phosphoric or phosphonic acid wherein each alkyl residue comprises from 1 to 10 carbon atoms.

15. The process according to claim 12, wherein, in (i), the following atomic or molar ratios are used:
Si/Al from 10/1 to 250/1, tetra-alkyl ammonium hydroxide/Si from 0.05/1 to 0.2/1, $H_2O$/Si from 5/1 to 40/1, and P/Al from 0.1 to 5.0.

16. The process according to claim 12, wherein in (i), the mixture is heated to a temperature ranging from 30 to 80 °C. until a limpid solution is obtained.

17. The process according to claim 12, wherein, in (ii), said heating is effected at a pH ranging from 11 to 12 and to a temperature ranging from 60 to 120° C., operating in a closed vessel at autogenous pressure of the system, or at atmospheric pressure with refluxing, for a time ranging from 10 minutes to 3 hours.

18. The process according to claim 12, wherein, in (ii), an alcohol, having from 1 to 10 carbon atoms, is added to the mixture up to an alcohol/Si ratio of 8/1.

19. The process according to claim 12, further comprising aging the gel for 1 to 24 hours at the end of (iii).

20. A process for the preparation of a solid composition comprising
from 30 to 99% by weight of the amorphous solid according to claim 1, and
from 70 to 1% by weight of an inert inorganic binder, the process comprising:
forming a mixture that comprises the from 30 to 99% by weight of the amorphous porous solid, and the from 70 to 1% by weight of an inert inorganic binder 21. The process according to claim 20, wherein said porous solid is in the form of a humid gel and is mixed with said binder with a weight ratio between the binder and the gel ranging from 0.05 to 0.5.

22. The process according to claim 20, wherein said mixture also comprises a plasticizing agent selected from methyl cellulose, stearine, and glycerol.

23. The process according to claim 20, wherein an organic acid is added to said mixture in a quantity ranging from 0.5 to 8 g per 100 g of binder.

24. The process according to claim 20, wherein said mixture is homogenized by mixing and heating to a temperature ranging from 40 to 90° C., until a paste is obtained, the paste is then extruded into cylindrical granules having a size of 2-10 mm in length and 0.5-4.0 mm in diameter, and is finally dried and calcined.

* * * * *